United States Patent
Gada et al.

(10) Patent No.: US 8,545,742 B2
(45) Date of Patent: Oct. 1, 2013

(54) METHOD OF FABRICATING A LOW CRYSTALLINITY POLY(L-LACTIDE) TUBE

(75) Inventors: Manish B. Gada, Santa Clara, CA (US); Lothar W. Kleiner, Los Altos, CA (US); Bethany E. Steichen, San Francisco, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 279 days.

(21) Appl. No.: 12/550,153

(22) Filed: Aug. 28, 2009

(65) Prior Publication Data
US 2011/0049751 A1    Mar. 3, 2011

(51) Int. Cl.
*B29C 47/10*  (2006.01)
(52) U.S. Cl.
USPC ............. 264/209.5; 264/209.1; 623/1.38
(58) Field of Classification Search
USPC .............. 264/209.1, 209.5; 623/1.38
See application file for complete search history.

(56) References Cited

U.S. PATENT DOCUMENTS

| | | | |
|---|---|---|---|
| 5,538,411 A * | 7/1996 | Gates ...................... 425/133.1 |
| 6,345,972 B1 | 2/2002 | Guillemette |
| 6,669,458 B2 | 12/2003 | Guillemette et al. |
| 6,692,804 B1 | 2/2004 | Guillemette et al. |
| 6,902,388 B2 * | 6/2005 | Guillemette et al. ......... 425/190 |
| 6,971,865 B2 | 12/2005 | Prue |
| 2006/0020330 A1 * | 1/2006 | Huang et al. ................ 623/1.49 |
| 2010/0252965 A1 * | 10/2010 | Wang et al. .................. 264/563 |

OTHER PUBLICATIONS

Osswald, Tim A. "Polymer processing fundamentals" 1998 (pp. 70-71).*
Cross Head Extrusion, process, downloaded from www.extrudedprofilesworld.com/cross-head-extrusion.html, May 27, 2009, 2 pgs.

* cited by examiner

*Primary Examiner* — Robert J Grun
(74) *Attorney, Agent, or Firm* — Squire Sanders (US) LLP

(57) ABSTRACT

Methods of fabricating a low crystallinity polymer tube for polymers subject to strain-induced crystallization. The low crystallinity tube may be further processed to make an implantable medical device.

12 Claims, 5 Drawing Sheets

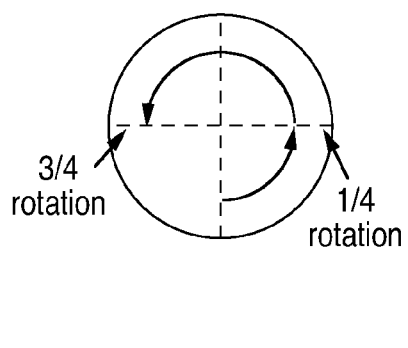
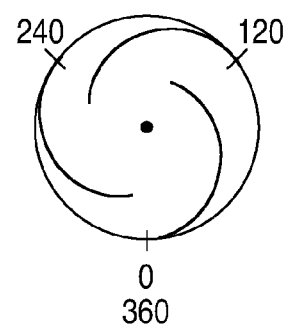
FIG. 8A                 FIG. 8B
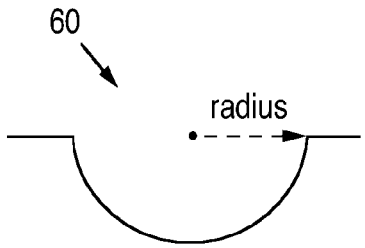
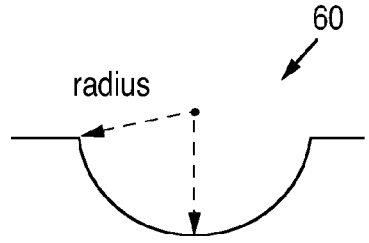
FIG. 9A                 FIG. 9B
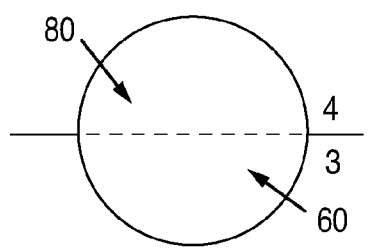
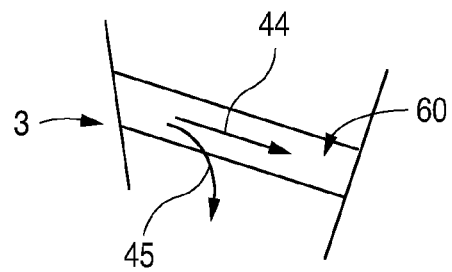
FIG. 9C                 FIG. 11
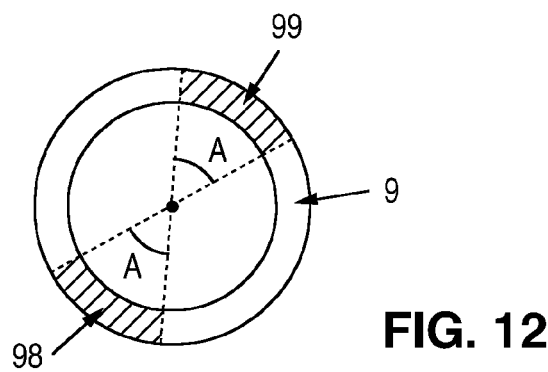
FIG. 12

METHOD OF FABRICATING A LOW CRYSTALLINITY POLY(L-LACTIDE) TUBE

BACKGROUND OF THE INVENTION

1. Field of the Invention

This invention relates to methods of manufacturing polymeric medical devices, in particular, stents.

2. Description of the State of the Art

The discussion that follows is intended solely as background information to assist in the understanding of the invention herein; nothing in this section is intended to be, nor is it to be construed as, prior art to this invention.

Until the mid-1980s, the accepted treatment for atherosclerosis, i.e., narrowing of the coronary artery(ies) was coronary by-pass surgery. While effective and having evolved to a relatively high degree of safety for such an invasive procedure, by-pass surgery still involves serious potential complications and in the best of cases, an extended recovery period.

With the advent of percutaneous transluminal coronary angioplasty (PTCA) in 1977, the scene changed dramatically. Using catheter techniques originally developed for heart exploration, inflatable balloons were employed to re-open occluded regions in arteries. The procedure was relatively non-invasive, took a very short time compared to by-pass surgery and the recovery time was minimal. However, PTCA brought with it another problem, elastic recoil of the stretched arterial wall which could undo much of what was accomplished and, in addition, failed to satisfactorily ameliorate another problem, restenosis, the re-clogging of the treated artery.

The next improvement, advanced in the mid-1980s was use of a stent to scaffold the vessel wall in place after PTCA. This, for all intents and purposes, put an end to recoil, but did not entirely resolve the issue of restenosis. That is, prior to the introduction of stents, restenosis occurred in from 30-50% of patients undergoing PTCA. Stenting reduced this to about 15-20%, much improved, but still more than desirable.

In 2003, drug-eluting stents or DESs were introduced. The drugs initially employed with the DES were cytostatic compounds, compounds that curtailed the proliferation of cells that resulted in restenosis. The occurrence of restenosis was thereby reduced to about 5-7%, a relatively acceptable figure. Today, the DES is the default industry standard for the treatment of atherosclerosis and is rapidly gaining favor for treatment of stenoses of blood vessels other than coronary arteries such as peripheral angioplasty of the superficial femoral artery.

The next generation of stents will be those designed to be biodegradable. Although bioerodable metals may be used, biodegradable polymers are often used for fabrication of such a stent. However, there are potential shortcomings in the use of polymers as a material for implantable medical devices, such as stents. The strength to weight ratio of polymers is usually smaller than that of metals. Also, certain polymers have low toughness, i.e. are brittle. Semicrystalline polymers in particular are useful as stent material. However, they must be processed in a manner that provides high strength and fracture toughness.

SUMMARY OF THE INVENTION

Various embodiments of the present invention include a method of fabricating an implantable medical device, such as a stent. The method includes, but is not limited to, performing the following operations: heating and mixing a polymer or a polymer blend, optionally with other materials, in an extruder to form a polymer melt; forming a tube from the polymer melt using the extruder and a die assembly in which the polymer melt flows in a spiral motion through at least part of the die assembly, and wherein the crystallinity of the polymer in the formed tube is not more than 5%; processing the polymer tube at a temperature below the melting temperature ($T_m$) of the polymer to increase the radial strength of the polymer tube and increase the crystallinity of the polymer tube between about 20% and about 50%; and forming a stent from the processed polymer tube.

In some embodiments, the spiral flow results from the die assembly used. The die assembly comprises a passage way from inlet to outlet and at least a portion of the passage way is formed by cooperative engagement of first and second conical surfaces, or substantially conical surfaces. The spiral flow of the polymer melt results from flow through a plurality of grooves in at least one of the conical surfaces, and at least one of the grooves forms a portion of a conical helix.

In some embodiments, forming an implantable medical device, such as a stent, from the polymer tube includes radially expanding the polymer tube at a temperature between the glass transition temperature ($T_g$) and the melting temperature of the polymer, and forming a stent from the processed tube.

In some embodiments, the polymer is poly(L-lactide), and the polymer tube is processed by radial expansion at a temperature in the range of 60° C. to 100° C.

Other methods of fabricating an implantable medical device are encompassed by the various embodiments of the present invention. The methods include, but are not limited to, the following operations: heating and mixing a polymer or a polymer blend, optionally with other materials, in an extruder to form a polymer melt; and forming a tube from the polymer melt such that the polymer of the formed tube has a crystallinity of not more than 5%. The tube is formed using the extruder and a die assembly wherein when the polymer melt has a velocity component in the azimuthal direction during at least a portion of the time that the polymer flows through an annular portion of the die assembly.

BRIEF DESCRIPTION OF THE DRAWINGS

FIGS. 8A and 8B depict top-views illustrating aspects of a part of a die assembly useful in performing the methods of the present invention.

FIGS. 9A, 9B, and 9C depict the cross-section of grooves in part of a die assembly useful in performing the methods of the present invention. p

FIG. 11 depicts the flow pattern of a polymer melt in a spiral groove.

FIG. 12 depicts the distribution of polymer melt around an annular passage way of a die assembly.

DETAILED DESCRIPTION OF THE INVENTION

Figure 1:
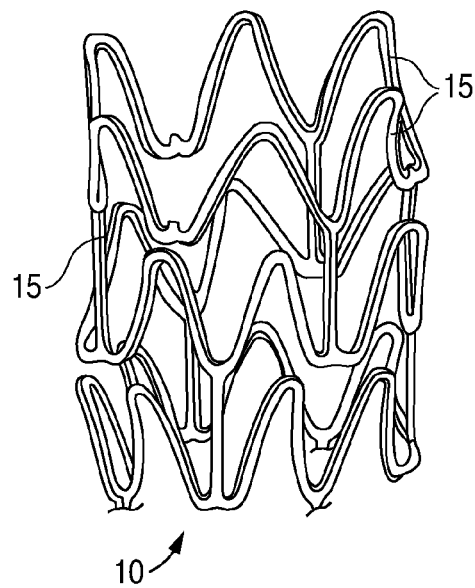
FIG. 1 depicts a stent.

Use of the singular herein includes the plural and vice versa unless expressly stated to be otherwise. That is, "a" and "the" refer to one or more of whatever the word modifies. For example, "a tube" includes one tube, two tubes, etc. Likewise, "a polymer" may refer to one, two or more polymers, and "the polymer" may mean one polymer or a plurality of polymers. By the same token, words such as, without limitation, "tubes" and "polymers" would refer to one tube or polymer as well as to a plurality of tubes or polymers unless, again, it is expressly stated or obvious from the context that such is not intended.

As used herein, any ranges presented are inclusive of the end-points. For example, "a temperature between 10° C. and 30° C." or "a temperature from 10° C. to 30° C." includes 10° C. and 30° C., as well as any temperature in between.

As used herein, unless specifically defined otherwise, any words of approximation such as without limitation, "about," "essentially," "substantially" and the like mean that the element so modified need not be exactly what is described but can vary from the description by as much as ±15% without exceeding the scope of this invention.

As used herein, the use of "preferred," "preferably," or "more preferred," and the like to modify an aspect of the invention refers to preferences as they existed at the time of filing of the patent application.

This invention relates to medical devices, and particularly, implantable medical devices. Implantable medical devices include appliances that are totally or partly introduced, surgically or medically, into a patient's body or by medical intervention into a natural orifice, and which are intended to remain there after the procedure. Examples of implantable medical devices include, without limitation, implantable cardiac pacemakers and defibrillators; leads and electrodes for the preceding; implantable organ stimulators such as nerve, bladder, sphincter and diaphragm stimulators, cochlear implants; prostheses, vascular grafts, self-expandable stents, balloon-expandable stents, stent-grafts, grafts, artificial heart valves, closure devices for patent foramen ovale, vascular closure devices, cerebrospinal fluid shunts, and intrauterine devices.

More particularly, this invention is directed to stents, a type of implantable medical device. Although the discussion that follows focuses on a stent as an example of an implantable medical device, the embodiments described herein are easily applicable to other implantable medical devices.

Stents are generally cylindrically shaped devices that function to hold open, and sometimes expand, a segment of a blood vessel or other anatomical lumen such as urinary tracts and bile ducts. A "lumen" refers to a cavity of a tubular organ such as a blood vessel. Stents are often used in the treatment of atherosclerotic stenosis in blood vessels. "Stenosis" refers to a narrowing or constriction of a bodily passage or orifice. "Restenosis" refers to the reoccurrence of stenosis in a blood vessel or heart valve after it has been treated (as by balloon angioplasty, stenting, or valvuloplasty) with apparent success. In treatment of stenosis, stents reinforce body vessels and prevent restenosis following angioplasty in the vascular system. In addition to treatment for coronary artery disease such as atherosclerosis and restenosis, stents may be used for the maintenance of the patency of a vessel in a patient's body when the vessel is narrowed or closed due to diseases or disorders including, without limitation, tumors (in, for example, bile ducts, the esophagus, the trachea/bronchi, etc.), benign pancreatic disease carotid artery disease, peripheral arterial disease (PAD), and vulnerable plaque. For treatment of PAD, stents may be used in peripheral arteries such as the superficial femoral artery (SFA). Use of stents in the SFA appears to be more challenging than in coronary vessels and in other peripheral vascular beds, such as the iliac and carotid arteries.

Stents are typically composed of scaffolding that physically holds open and, if desired, expands the wall of a passage way. FIG. 1 depicts an example of a three-dimensional view of a stent 10. In some embodiments, a stent may include a body, backbone, or scaffolding having a pattern or network of interconnecting structural elements or struts 15. In general, the body of a medical device may be the device in a functional form, but prior to the application of a coating or other material different from that of which the device body is formed. The embodiments disclosed herein are not limited to stents or to the stent pattern illustrated in FIG. 1. The structural pattern of the device, including a stent, can be of virtually any design.

A stent such as stent 10 may be fabricated from a polymeric tube, or a sheet by rolling and bonding the sheet to form a tube. A tube or sheet can be formed by extrusion or injection molding. A stent pattern, such as the one pictured in FIG. 1, can be formed in a tube or sheet with a technique such as laser cutting or chemical etching.

Typically, stents are capable of being compressed, or crimped, onto a catheter so that they can be delivered to, and deployed at, a treatment site. Delivery includes inserting the stent through small lumens using a catheter and transporting it to the treatment site. Deployment includes expanding the stent to a larger diameter once it is at the desired location.

The stent must be able to satisfy several mechanical requirements. First, the stent must be capable of withstanding the structural loads, namely radial compressive forces, imposed on the stent as it supports the walls of a vessel lumen. This requires a sufficient degree of strength and rigidity or stiffness. In addition to having adequate radial strength, the stent should be longitudinally flexible to allow it to be maneuvered through a tortuous path and to enable it to conform to a deployment site that may not be linear or may be subject to flexure. The material from which the stent is constructed must allow the stent to undergo expansion which typically requires substantial deformation of portions of the stent. Once expanded, the stent must maintain its size and shape throughout its service life despite the various forces that may come to bear thereon, for example and without limitation, the cyclic loading induced by the beating heart. A stent must be capable of exhibiting relatively high toughness or resistance to fracture. For stents used in the SFA, the mechanical requirements can be higher than for stents in coronary arteries as the SFA is subjected to various forces, such as compression, torsion, flexion, extension, and contraction, which place a high demand on the mechanical performance of implants.

Although stents made of nonerodible metals and metal alloys have become the standard of care for treatment of artery disease, it is desirable to make stents out of biodegradable polymers. In many treatment applications, the presence of a stent in a body is necessary for a limited period of time until its intended function of, for example, maintaining vascular patency and/or drug delivery is accomplished. Therefore, a device body, including the scaffolding of a stent, may be fabricated from biodegradable, bioabsorbable, and/or bioerodable polymers and can be configured to partially or completely erode away after the clinical need for them has ended.

The duration during which the device maintains luminal patency depends on the bodily disorder that is being treated. If a drug is included in the device, the duration of drug delivery may be the same as or may differ from the duration during which luminal patency is maintained. For example, in treatments of coronary heart disease involving use of stents in diseased vessels, the duration can be in a range from several months to a few years. The duration is typically up to about six months, twelve months, eighteen months, or two years. In some situations, the treatment period can extend beyond two years. As another example, in treatments of SFA, the duration can be in a range from one or two months to several years. For SFA, the duration is typically up to up to about six months, twelve months, eighteen months, or two years. Preferably luminal patency is maintained for a time period between about 6 months and about 8 months.

Although biodegradable polymers can de designed to erode away, as noted above, one drawback of polymers as compared to metals and metal alloys is that the strength to weight ratio of polymers is usually smaller than that of metals. To compensate for this, a polymeric stent can require significantly thicker struts than a metallic stent, which results in an undesirably large profile. One way of addressing the strength deficiency of polymers is to process the polymer in a manner that improves its strength and toughness. The strength and toughness of a polymer is a complex function of the morphology of the polymer, particularly if the polymer is a semicrystalline polymer. Semicrystalline polymers with high strength and toughness can be achieved by orienting the polymer chains, particularly in a biaxial orientation, having small crystalline domains, and a high crystal density.

Polymer chain orientation may be obtained by deforming the polymer. Deforming polymers tends to increase the strength along the direction of deformation (strain), which is believed to be due to the induced polymer chain orientation along the direction of deformation. For example, a polymer tube can be fabricated to obtain a biaxial orientation by both axial and radial deformation of the polymer tube. The radial expansion of a tube provides preferred circumferential polymer chain orientation in the tube, and stretching a tube provides preferred axial orientation of polymer chains in the tube. The ratio of radial to axial orientation must be optimized for a particular stent design to obtain desirable mechanical properties.

As noted above, another way to improve fracture toughness is by reducing the size of the polymer crystals and increasing the density of the nuclei from which the crystals grow. Smaller crystals lead to more tie chains between crystals, that is polymer chains that are part of both crystals. The amorphous regions between crystals contribute to strength and fracture toughness. Also, crystals or crystalline regions act analogously to physical cross-links and increase modulus. However, if the crystallinity is too high, then fracture toughness and elongation are reduced. Thus, some crystallinity is desirable, but not so much that the polymer becomes brittle. Many small crystalline regions are preferable to fewer larger crystalline regions. A combination of high crystal density and small crystal size is preferred.

Crystal size and density, as well as the total crystallinity, are a result of the temperature and processing history of the polymer. For a polymer, crystallization generally tends to occur at temperatures between the glass transition temperature, $T_g$, and the melting temperature, $T_m$, of the polymer. At temperatures close to $T_g$ the rate of crystal nucleation rate is greater then the rate of crystal growth. At temperatures closer to $T_m$, the rates are reversed with the rate of crystal growth being greater than the rate of crystal nucleation. Processing also impacts polymer crystallinity. Deformation or shear in a polymer melt tends to extend the polymer chains in the direction of shear or strain. If sufficiently deformed, the crystallinity may result from strain-induced crystallization as a result of extension and alignment of the polymer chains.

Biaxial orientation and increased crystallinity may be obtained by radially and axially expanding a polymer tube at controlled temperature. Expansion may be performed at a temperature between $T_g$ and $T_m$ at a temperature where the rate of crystal nucleation is greater than crystal growth. The resulting polymer tube has biaxial orientation and crystallinity of the desired morphology. In particular, the crystalline regions formed by biaxial orientation have a "shish-kebab form" that differs from the typical spherulitic form that would result from crystallization from a quiescent polymer melt. It is believed that these shish-kebab crystalline regions result in superior mechanical properties as compared to the spherulitic form.

Thus, optimization of the strength and fracture toughness of a semicrystalline polymer is not a simple process, but is a complex function of both processing and temperature. Careful control of the processing and temperature conditions of the polymer allow one to obtain a polymer with the desired morphology, that is the desired crystal size, density, and orientation, to maximize both strength and toughness. Conventional extruded semicrystalline polymer tubes may have crystallinity due to the manner of processing. The crystalline morphology of the crystalline regions of the as extruded tube differs from the crystallinity formed by the biaxial expansion operation. It is desirable to have all of the crystalline regions of the desired morphology formed in one step in the biaxial expansion. Thus, it is desirable to start with an extruded polymer tube of low or no crystallinity which will allow for all the crystallinity of the tube to be formed in one step under controlled conditions. Ideally, the polymer of the extruded polymer tube would be completely amorphous, but in practice this is not easily achieved. A stent manufactured from a polymer tube for which the crystallinity is formed in one step is expected to have superior mechanical properties compared to one manufactured from a polymer tube for which some crystallinity resulted from prior processing such as the extrusion process.

The various embodiments of the present invention provide methods of extruding a polymer of low crystallinity. Although reference will be made to a polymer tube, the embodiments of the present invention are not so limited, and all polymer constructs are encompassed. As used herein, "polymer construct" refers to any useful article of manufacture made of a polymer, a polymer formulation, or a blend of polymers, that is used as a starting material for further manufacturing steps in the fabrication of a medical device, including an implantable medical device. Non-limiting examples of polymer constructs include a tube, a sheet, a fiber, etc. A polymer construct is not a scaffolding structure.

A polymer tube may be used in the fabrication of an implantable medical device, such as a stent. Some of the process operations involved in fabricating a polymeric stent may include:

(1) forming a polymeric tube using extrusion;
(2) radially and/or axially deforming the formed tube by application of heat and/or pressure;
(3) forming a stent from the deformed tube by cutting a stent pattern in the deformed tube such as with chemical etching or laser cutting;
(4) coating the stent with a coating including an active agent;

(5) crimping the stent on a support element, such as a balloon on a delivery catheter;

(6) packaging the crimped stent/catheter assembly; and (7) sterilizing the stent assembly.

In some embodiments of the present invention, a method is provided which results in the polymer of the extruded polymer tube that is completely amorphous (100% amorphous, 0% crystallinity) or with very low crystallinity, such as less than 5% crystallinity. Embodiments of the present invention encompass a crystallinity of not more than 1%, not more than 2%, not more than 4%, and not more than 5% in the polymer of the polymer tube. In some other embodiments, the crystallinity of the polymer may be greater than 5%, for example between about 5% and about 10%. However, a crystallinity of less than 5% is preferred, and is expected to result in superior mechanical properties of a device, such as a stent, fabricated from the tube of such a polymer.

Figure 2:
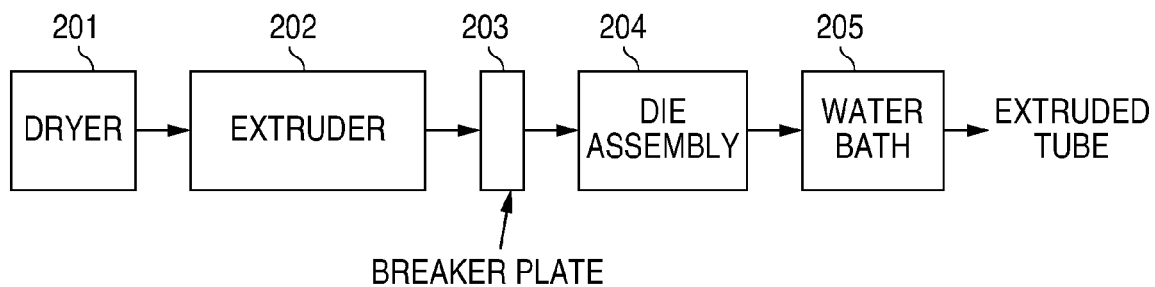
FIG. 2 depicts a flow chart of a conventional extrusion process.

As noted above, the tube is typically formed by extrusion. Extrusion refers to the process of conveying a polymer melt through an extruder and forcing the polymer melt through a die that imparts a selected shape to the polymer exiting the extruder. FIG. 2 illustrates a typical extrusion process for extrusion of a polymer tube. The polymer as received, typically in the form of pellets or granules, is dried in a dryer (201) or hopper dryer before being conveyed to the extruder (202) which melts the polymer to form a polymer melt which is then forced through a breaker plate (203) before being forced through the die which is part of the die assembly (204) to form a cylindrical film in the shape of a tube. The film is cooled in a water bath (205) and drawn axially to form the final tube product. Although illustrated as a line of equipment in FIG. 2, the individual pieces of equipment in the equipment train are not necessarily arranged in a line. Although FIG. 2 includes a water bath for cooling, other manners of cooling the extruded tube may be used and are encompassed within the scope of the present invention.

An extruder generally includes a barrel through which a polymer melt is conveyed from an entrance to an exit port. The polymer can be fed to the extruder barrel as a melt or in a solid form below its melting temperature. If solid polymer is used, the solid polymer is melted as it is conveyed through the barrel. The polymer in the extruder barrel is heated to temperatures above the $T_m$ of the polymer and exposed to pressures above ambient (greater than 1 standard atmosphere). The polymer within the barrel is conveyed or pumped, for example, through the use of rotating screws or a rotating screw. Representative non-limiting examples of extruders for use with the present invention may include single screw extruders, intermeshing co-rotating and counter-rotating twin-screw extruders and other multiple screw plasticating extruders. A typical single screw extruder has three sections, a feeding section, a compression section, and a metering section.

The polymer melt exits the extruder through a breaker plate to a die placed at the end of the extruder barrel. The breaker plate, often used in conjunction with a screen, removes lumps, such as unmelted polymer. A die generally refers to a device having an orifice with a specific shape or design geometry that it imparts to a polymer melt pumped from an extruder. In the case of tubing extrusion, the die has a circular-shaped orifice that imparts a cylindrical shape to the polymer melt exiting the die.

After the polymer leaves the die, it swells due to the fact that, unlike a non-polymeric liquid such as water, the response of a polymer melt to shear has a normal stress component which is due to stored elastic energy. This normal stress component is no longer constrained by the wall when it exits the die, resulting in die swell. As the polymer leaves the die, it is stretched and drawn down by a conveyor or puller during cooling. "Draw down" refers to reducing the size of the polymer by stretching. For example, a tube is stretched longitudinally which reduces the diameter of the tube. The amount of draw down is defined as the "draw down ratio," which is the ratio of the area of the die opening to the final cross-sectional area of the tube. The draw down ratio may be at least three times the original extruded shape. In some embodiments, the polymeric tube is drawn so that a diameter of the formed tube is less than a target diameter, such as for example, the diameter of a lumen in which the device is intended to be deployed.

Extruded polymer tubes made of semicrystalline polymers may have widely variable crystallinity. As used herein, reference to a tube with a crystallinity of X % will mean that the polymer of the tube has a crystallinity of X %. For example, the inventors found that extrusion of tubes of the polyester poly(L-lactide) (PLLA) in a 1" Killion single screw extruder at about 10 RPM, followed by cooling in a water bath, resulted in a polymer tube of 17-24% crystallinity. Variation of the processing parameters including the temperature profile of the extruder, screw speed, screw design, tubing cooling rate via changes in the temperature of the water bath, and the air gap, that is the distance between the die exit and the water bath, the puller speed, the air pressure in the extruder, and the area draw down ratio did not result in tube with a crystallinity outside the range of 17-24%. Thus, a polymer tube of low crystallinity is not easily obtained, and is not obtained by using just any extrusion equipment and process.

The source of crystallinity in an extruded polymer tube is a complicated function of polymer morphology in the extruder, the Theological properties of the polymer, the conditions in the extruder such as the temperature and pressure, and the several parameters in the extrusion process. The presence of unmelted crystals in a polymer melt exiting a die is one source of crystallinity in a formed polymer tube. For complete removal of the crystalline phase from the polymer, the temperature should be high enough to melt the crystal, but below a temperature that would degrade the polymer. The melting efficiency can be facilitated by optimizing screw geometry. Other sources of crystallinity in an extruded tube are insufficient homogeneity of the polymer melt and chain orientation in the polymer melt in the extruder, and/or in the polymer melt exiting the extruder. Quenching of the polymer film exiting the die may inhibit or prevent crystal growth. Quenching of the film refers to an extremely rapid cooling or extremely rapid reduction of the temperature of the polymer from a temperature above $T_m$ of the polymer to below $T_g$ of the polymer.

The inventors observed that PLLA tubes extruded using an alternative die assembly that imparts a spiral flow to the polymer melt unexpectedly resulted in a tube with a crystallinity of not more than 4% or about 4%. The polymer resin was dried before being extruded in a Killion 1" extruder through the alternative die assembly, and an annular die before being cooled in a water bath at either ambient (about 20 to 25° C.) or chilled (about 15° C. or lower). The extrusion experiments are summarized in Example 1. It is believed the alternative die assembly resulted in the lower crystallinity. Although polymer tubes manufactured from such die assemblies were known to exhibit enhancement of bending strength and durability, the low crystallinity was unexpected.

The alternative die assembly that was used is a spiral cross-head design of Guill Tool and Engineering. Examples of these die assemblies and/or subassemblies thereof, are described in U.S. Pat. Nos. 6,902,388, and 6,345,972, both of which are incorporated by reference as if fully set forth, including any drawings, herein. The die assembly is designed to provide a balanced flow through the die. A balanced flow means that the polymer melt has a uniform temperature and a uniform melt conformation, and is distributed evenly about the circumference of an annular passage way, or extrusion channel, leading to the outlet and the die. An uneven distribution would lead to a tube with variable wall thickness around the circumferences, such as thicker walls on one side of the tube than the side that is 180° opposite. In addition, the die assembly, which includes the die, is designed such that the polymer melt undergoes a spiral motion as it flows through the die assembly. It is believed that a die assembly or a cross-head die assembly with an even distribution of the polymer melt, or an essentially even distribution of the polymer melt, in the flow passage way, and especially one that imparts a spiral or rotational component to the flow of the polymer melt, produces a tube of low crystallinity, particularly, in the section leading up to the die, such as less than 5%.

Figure 3:
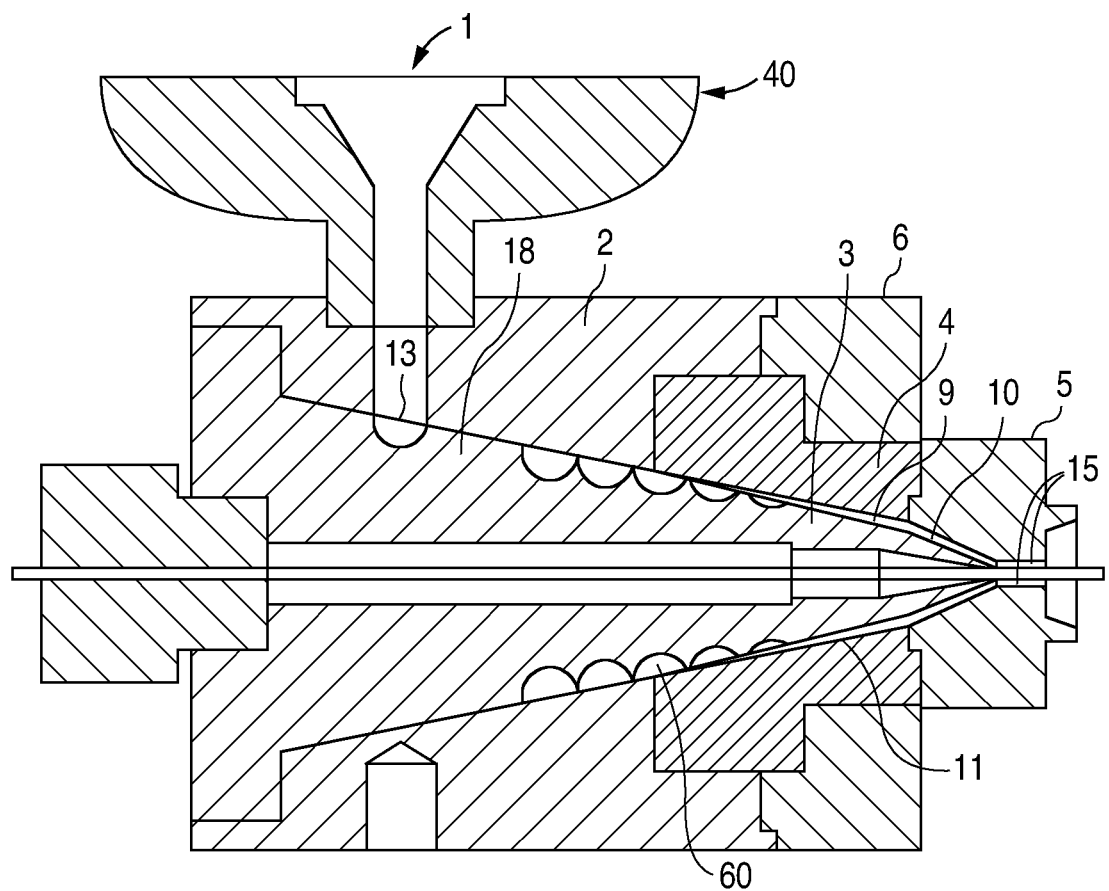
FIG. 3 depicts a die assembly useful in performing the methods of the present invention

An example of a die assembly useful in performing the methods of the present invention is shown in FIG. 3. As illustrated in FIG. 3, the polymer melt is received at inlet 13 from an extruder outlet 40 and is supplied to a tapered annular extrusion passage way 9. The general function of the die assembly is to receive the polymer melt at the upstream inlet 13 and distribute it to downstream outlet 15 in a flow pattern that is evenly distributed about the extrusion passage way 9. Flow channels that are not shown take the polymer melt from the inlet 13 to the grooves 60 in the tip 3 which merge with the annular extrusion passage way 9 leading to the outlet 15.

The extrusion passage way 9 depicted in FIG. 3 is formed between the surface 10 of tip 3 and surface 11 of the die holder 4. Tip 3 fits into bore 18 of die body assembly 2. A die 5 may be removably fixed to the die holder 4 to form a die module and complete the extrusion passage way 9, and form the exit 15. A cap 6 keeps the components of the die assembly securely assembled. The bolts or other fasteners holding the components together are not illustrated in FIG. 3. The extrusion passage way 9 does not have a constant cross-section. The annular extrusion passage way is a tapering annular passage way. The passage way is essentially the space between two parts in the shape of conical sections, substantially in the shape of conical sections, or in a shape similar to conical sections. The clearance between surfaces 10 and 11 also varies from the upstream end to the downstream end. Thus, for passage way 9 the internal and external radius of the annulus change and the difference between the internal and external radii also varies.

Figure 4:
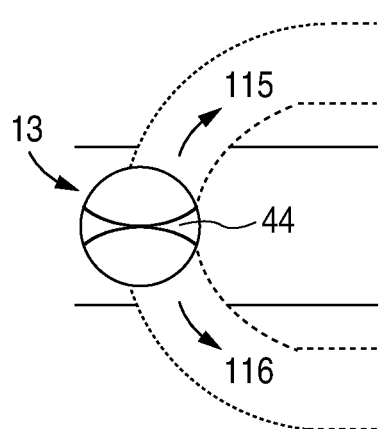
FIG. 4 depicts a top view of a representative inlet to a die assembly.

A continuous flow passage way is formed from inlet 13 to the outlet 15. The polymer melt is received from the extruder at inlet 13. As illustrated in FIG. 4, a representative and non-limiting top view, the polymer melt comes in inlet 13, flows down, and is divided into 2 primary flow channels 115 and 116. There is a dividing wedge 44 between the two channels to assure even distribution of the flow. The flow may be subsequently divided again in a like manner to yield 4 secondary flow channels, and again to form 8 tertiary channels, etc. Alternatively, the flow channel may be divided into 3 channels yielding 6 secondary flow channels. The primary, secondary, or tertiary, etc. flow channels end in grooves 60 in the tip 3 depicted in FIG. 3. The polymer melt flows through the grooves to the tapered annular extrusion passage way 9, also illustrated in FIG. 3. The polymer melt may be distributed among a number of flow channels leading to the spiral shaped grooves in another manner than that depicted in FIG. 4.

Figure 10:
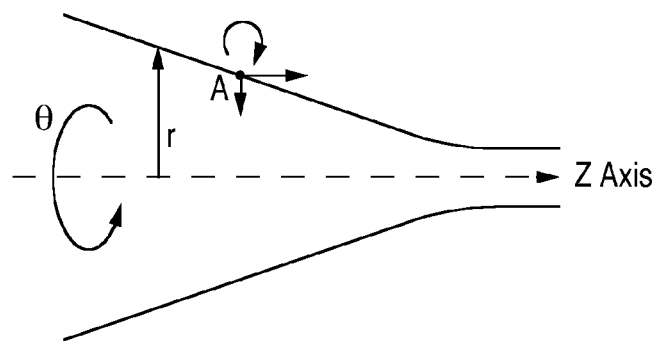
FIG. 10 depicts the vector components of the polymer melt velocity in cylindrical coordinates.
Figure 5:
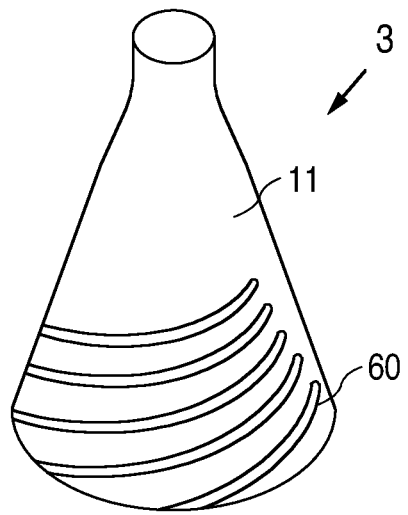
FIG. 5 depicts spiral grooves in part of a die assembly useful in performing the methods of the present invention.
Figure 13:
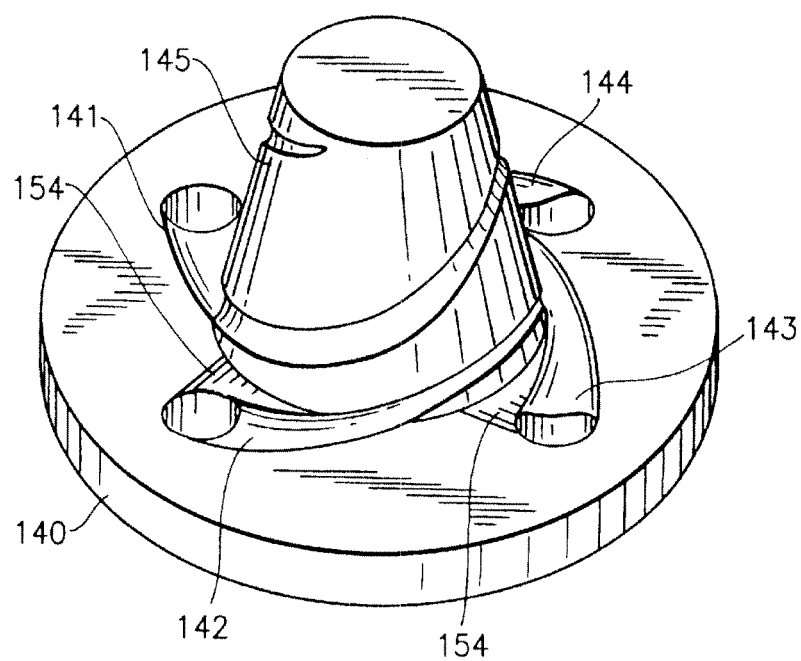
FIG. 13 depicts part of a die or a die tip that may be used with the embodiments of the present invention.

The semi-volute shaped grooves form spiral, or conical helical, flow channels in the face of the generally conically shaped tip 3. FIG. 5 illustrates the grooves 60 in the conical surface 11 of tip 3. The flow channels are grooves, continuous indentations, engravings, or channels formed in the surface. An alternative embodiment of a die or die tip with spiral grooves is shown in FIG. 13, which is a replication of FIG. 10 of U.S. Pat. No. 6,345,972. U.S Pat. No. 6,345,972 describes the die as follows:

. . . a series of symmetrically positioned (nested) semi-volute shaped grooves, 141, 142, 143, and 144 are constructed in the downstream face of a die module 140. The module 140 has a truncated conical mating surface 145 which mates with a complimentary surface of the immediately adjacent downstream module (not shown) to form an extrusion channel. The grooves 141-144 will therefore extend into the extrusion channel thus formed. A dam 154 separates the upstream end of each of the spiral grooves from the extrusion channel and tapers gradually downstream to encourage the spiral flow. It has been found that such a configuration will further balanced the flow of plastic evenly throughout the extrusion channel.

(U.S. Pat. No. 6,345,972, column 3, line 58 to column 4, line 4).

Figure 6A:
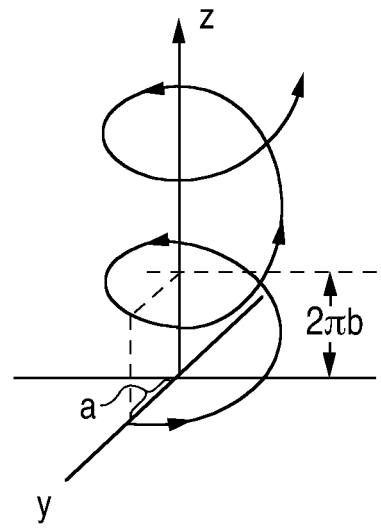
FIGS. 6A and 6B depict helices in Cartesian and cylindrical coordinates.
Figure 6B:
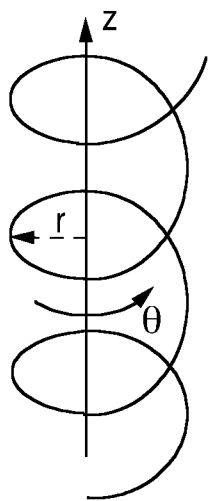
Figure 7:
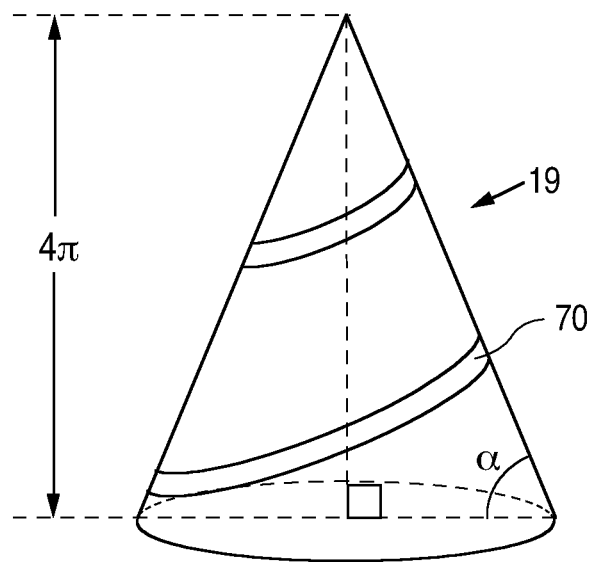
FIGS. 7 depicts a conical helix on the face of a cone.

The spiral grooves illustrated in FIG. 5 may be generally expressed by the mathematical formula for a conical helix. FIG. 6A depicts a helix of radius a and pitch of 2πb which is represented is mathematically in an x-y-z space as x(t)=a cos(t), y(t)=a sin(t), and z=b(t) where z is the height and x-y form a plane perpendicular to z. FIG. 6B depicts a helix of pitch 2π and radius 1 in polar coordinates which is represented mathematically by r(t)=1, z(t)=t, and θ(t)=t. The "pitch" is the height traveled in one complete rotation, that is the vertical distance traveled before x and y return to the initial value, or in polar coordinates, for θ to return to the initial value. Depicted in FIG. 7 is a conical helix 70 formed on the surface of a cone 19. The difference between a helix and a conical helix is that the radius changes for a conical helix as opposed to having a constant value. The conical helix 70 shown in FIG. 7 is formed on a cone 19 of slant angle α and height 4π, for which radius, r, at any point is related to the distance along the z-axis by tan α. The conical helix of pitch 2π shown in FIG. 7 corresponds to the mathematical formula r(t)=(tan α)/t, z(t)=t, and θ(t)=t. If the grooves 60 shown in FIG. 5 are not made in the surface of a mathematically true cone, the grooves would not form a true conical helix, but a similar path in which the radius of the helix varies with the height of the helix in the same manner as the radius of the tip 3 varies with the height of tip 3.

The grooves 60 are arranged symetrically around the circumference of the tip 3. In some embodiments, the number of grooves corresponds to the number of secondary, tertiary, etc. flow channels resulting from the division of the initial flow of the polymer melt from the extruder. In some embodiments, one or more of the grooves go completely around the tip, that is at least one complete rotation. In other embodiments, one or more of the grooves do not completely encircle the tip, that is do not form a complete rotation about the cone, but may cover about ¼ to about ¾ of a rotation as shown in a top view in FIG. 8A. Preferably the grooves overlap, that is for the 360° rotation, if one groove starts at 0° and ends at 130°, then the next groove would begin at 130° or less, such as 120° as illustrated in FIG. 8B. In some embodiments, one groove starts at the location around the circumference where a prior groove ends, such as when one groove starts at 0° and ends at 120°, then the next grooves starts at 120°. In some embodiments, the grooves do not overlap.

The cross-section of the grooves may be a semi-circle as depicted in FIG. 9A, essentially a semi-circle, or a circular segment, as depicted in FIG. 9B. The cross-section of the grooves may be other shapes. There may be similar mating grooves 80 in the surface of die holder 4 and die assembly body 2 such that when put together the grooves form a flow channel as illustrated in FIG. 9C. If the grooves are semi-circles in both die holder 4 and die assembly body 2, the flow channel formed is of circular cross-section. The combination of the surfaces forms the extrusion channel leading to the annular extrusion passage way 9. The grooves gradually taper as they move downstream, that is the cross-sectional area decreases in the direction of polymer flow, eventually reaching zero.

The spiral die assembly provides both a balanced flow and imparts a spiral or rotational component to the velocity of the polymer melt. It is believed that the tapering of the spiral grooves imparts a spiral flow or rotational velocity component to the polymer melt. The die assembly is intended to take molten polymer from the extruder and force it through a die, which is essentially an annulus, to form a hollow tube. The approximate shape of the flow passage way is illustrated FIG. 10 with a polar coordinate system. The z-axis is at the center of the die, and lies along the axis of the conical tip 3. At point A in FIG. 10 which is within a spiral flow channel, the velocity of the polymer melt has components in the z-direction, that is the polymer melt is flowing downstream to the annulus at the outlet. There is also a radial component inward as the flow passage way tapers to an annulus of a smaller diameter at the outlet. In addition, there is a azimuthal component θ, or rotational component. The azimuthal component is a result of forcing the polymer melt through the flow channels. It is believed that the low crystallinity results at least in part due to the rotational or azimuthal component of the flow in the section of the annular portion of the die assembly, and particularly if the rotational component of the flow occurs in a section just prior to or leading up to the die outlet.

The tapering spiral grooves also ensure a balanced flow of polymer melt in the annular portion of the die assembly. Balanced flow ensures polymer melt homogeneity. The polymer melt is forced through the spiral groove 60 in direction shown in FIG. 11 by arrow 44. As the grooves taper and merge with the annular extrusion passage way, some of the polymer melt is forced over the side of the grooves as illustrated in FIG. 11 by arrow 45. Thus, at the point where the grooves initially merge with the annular passage way 9, the polymer melt is at a high pressure and the clearance between surfaces 10 and 11 (see FIG. 3), or the width of the annular passage way 9, is small. The clearance increases as the grooves taper. As the polymer flows through the chamber, pressure losses result in a lower pressure further downstream. As a result, the tapering of the grooves and the increase in the clearance facilitate the even distribution of the polymer melt around the circumference of the annular passage way. The fact that the clearance is smaller upstream where there is a higher pressure limits the amount of polymer forced over the side, while further downstream where the pressure is lower, the clearance increases and the groove depth decreases, allowing approximately the same amount of polymer to go over the side of the channel.

Balanced flow means the polymer melt is distributed evenly around the circumference of the passage way, and that the melt has a uniform temperature and a uniform melt conformation. As FIG. 12. illustrates a top-view of annular passage way 9, the mass flow rate of polymer melt through a circular section 99 of angle A is the same, or substantially the same, as the mass flow through any other circular section of angle A, such as that of section 98. If the polymer flow is unevenly distributed, the wall of the tube extruded may vary in thickness around it's circumference.

It is believed that the combination of the balanced flow and the spiral or rotational flow result in the polymer tube of low crystallinity. Generally, the application of shear to a polymer melt results in orientation of the polymer chains in the direction of the shear. Thus, the polymer chains are in an extended configuration. If the polymer chains are in an extended configuration as they exit the die, the chains are more likely to crystallize when quenched than if the polymer chains are in a random coil configuration, a state in which the chains are not extended. It is entropically more favorable for rigid linear molecules, or rigid rods, to align and form a crystalline region, than to assume a random orientation with respect to each other. If the extended chains do not relax to their random coil configuration prior to quenching, the polymer chains are essentially rigid rods and crystallization is favored. If the polymer melt is subjected to further strain such as by pulling, the probability of crystallization increases. The stretching of polymer chains, such as in a draw down process, to form any chain orientation before/after exiting the die would cause strain-induced crystallization upon solidification of the polymer.

It is believed that the spiral flow, or rotational motion of the polymer melt, results in the chains exiting the die in a configuration that is the random coil configuration, or a configuration that is close to the random coil configuration, in contrast to a configuration in which some of the chains are in the extended chain configuration. The relaxation time of the polymer melt, that is the time frame for the polymer to return to its relaxed or unconstrained random coil configuration can be determined using a capillary viscometer. Use of the spiral cross-head produced a polymer melt with a relaxation time that was significantly less than the polymer melt produced previously with the conventional equipment which did not have spiral flow channels. Therefore, it can be inferred that the polymer chains are closer to their random coil configuration. It is believed that the flow in the helical grooves is analogous to the rifling action in a gun barrel and imparts a spiral flow to the polymer melt. It is believed that the azimuthal component of the velocity of the polymer melt in the annular region of the die assembly prevents the chains from being fully extended along the z-axis, and as a result the chains are closer to the random coil configuration.

Further the spiral grooves confine the polymer within the groove until the grooves merge with the tapered annular extrusion passage way. When the tapered grooves merge with the annular extrusion chamber, the polymer melt begins to spill over the edge of the groove into the annulus and thus the direction of polymer flow changes as described above and illustrated in FIG. 11. It is also believed that this change in polymer flow direction helps prevent the full extension of the polymer chains. In some embodiments, the melt relaxation time of the polymer melt as it exits the die may be less than 90 seconds, preferably less than 60 seconds, or more preferably, less than 45 seconds.

The spiral flow cross-head die assembly provides for improved mixing of the polymer melt with fewer dead spots, that is spots in the passage way in which the polymer melt is stagnant. It is also believed that the spiral flow and the balanced flow result in a polymer melt that is more uniform in temperature. It is believed that the improved mixing and more uniform temperature of the polymer melt may allow for a lower temperature in the extruder and a lower compression ratio, that is the ratio of the channel depth of the extruder in the feeding section to the channel depth at the end of the compression section or the beginning of the metering section. The channel depth in the extrusion chamber is essentially the height of the screw flight for a single screw extruder. The lower temperature, and lower shear which is consequence of the lower compression ratio, results in less polymer degradation during the extrusion process. The polymer melt residence time in the spiral cross-head die assembly is lower than that of the previously used conventional die assembly, also resulting is less polymer degradation.

The lower crystallinity polymer tube produced may be a polymer construct from which an implantable medical device, such as a stent, may be fabricated. It is expected that the lower crystallinity of the extruded polymer tube may result in a polymeric device, such as a stent, with improved and more consistent mechanical properties. It is important that the crystallinity is formed in one step and at the same time during the biaxial deformation. The extruded tubes made with conventional equipment not only included about 17% to 24% crystallinity, but the crystals formed were of a spherulitic form. Improved mechanical properties may result from careful control of the orientation and size of the crystalline regions in the polymer that are formed in the expansion process. It is believed that a shish-kebab form for the crystalline regions that results from the bi-axial expansion of the tube provides superior mechanical properties as compared to the spherulitic form. Thus, it is of critical importance that the initial extruded polymer tube have little or no crystallinity.

The shish-kebab crystalline regions result from controlled axial and radial expansion of the extruded polymer tube at a controlled temperature below the $T_m$, and preferably between $T_g$ and $T_m$. The degree of radial deformation may be quantified by a blow-up ratio or radial draw ratio, expressed as a percent by:

$$100 * \frac{\text{Inside Diameter of Deformed Tube}}{\text{Original Inside Diameter of Tube}}$$

In some embodiments, the radial draw ratio of a polymeric tube for use in fabricating a stent may be between about 100% to 500%. Similarly, the degree of axial deformation may be quantified by an axial draw ratio, expressed as a percent by:

$$100 * \frac{\text{Length of Deformed Tube}}{\text{Original Length of Tube}}$$

In some embodiments the radial and axial deformation of the formed tube is such that that the deformed tube is of a target diameter, such as without limitation, the diameter of a lumen. Careful control of the rate of deformation and the temperature during deformation allows for control of the crystal growth so that the tube has the desired morphology as described above.

Another advantage of a polymer construct that is amorphous or very low crystallinity, is that it provides for greater reproducibility of a final processed polymer construct with respect to microstructure and mechanical properties. Microstructure includes crystal size, crystal density, crystal orientation, amorphous orientation, and crystal shape. Preferably, all the crystallinity is developed in one step, during deformation and/or expansion. Thus, it is preferable to start with a tube which is amorphous, or substantially amorphous.

As a non-limiting example a polymer tube may be extruded from PLLA where the PLLA is heated and mixed in the extruder to form a polymer melt before being extruded though an annular die that is part of a die assembly. The die assembly may be a spiral cross-head die assembly. The extruder may be operated at a compression ratio in the range of about 3.5:1 to about 2.75:1, and at a temperature in the range about 190° C. to about 225° C., or more narrowly, from about 190° C. to about 215° C. The temperature at the die outlet or within the die assembly may be from about 200° C. to about 230° C. The pressure in the extruder and die assembly may reach a maximum from about 4500 psi to about 5500 psi. Upon exiting the die, the polymer film may be drawn, and subsequently quenched, such as by being passed through a water bath at ambient (20° C. to 25° C.) or slightly chilled (10° C. to 15° C.). The formed polymer tube may have a crystallinity of less than 5%, or less than 4%, as determined by differential scanning calorimetry (DSC). The polymer tube of PLLA may be expanded at a temperature in the range of from about 60° C. to about 100° C., or from about 60° C. to about 80° C. The radial expansion under controlled temperature conditions is performed to increase the radial strength of the polymer tube and to increase the crystallinity of the polymer tube to about 20% to about 50%, or to about 30% to 45%. In some embodiments, the polymer tube may be both axially and radially expanded. A stent may be formed from the expanded PLLA tube. As another non-limiting example, the above process may be carried out with poly(L-lactide-co-glycolide) of 85 mol % lactide, and 15 mol % glycolide.

It is believed that the use of a die assembly which imparts a spiral flow or a rotational component to the velocity of the polymer melt may provide an extruded tube of low crystallinity, that is less than 5% or about 5%, for any semicrystalline polymer that is susceptible to strain induced crystallization. Representative semicrystalline polymers that may be used in embodiments of the present invention include, without limitation, polymers formed from L-lactide, glycolide, or combinations thereof such as 85 mol % lactide and 15 mol % glycolide, PLLA, polyglycolide (PGA), poly(L-lactide-co-glycolide) (PLGA), poly(L-lactide-co-caprolactone) (PLCL), and PLLA-b-poly(ethylene oxide) (PLLA-b-PEO).

Representative examples of other polymers that may be used in the various embodiments of the present invention, if they are subjected to strain induced crystallization, include, without limitation: poly(hydroxybutyrate), polyorthoesters, polyanhydrides, poly(glycolic acid), poly(glycolide), poly(L-lactic acid), poly(L-lactide), poly(D-lactic acid), poly(D-lactide), poly(caprolactone), poly(trimethylene carbonate), polyester amide, polyesters, polyolefins, polycarbonates, polyoxymethylenes, polyimides, polyethers, and copolymers and combinations thereof.

As Used Herein, the Following Definition Apply:

As used herein, when reference is made to a polymer having X mol % of a particular monomer such refers to the mole percent of the monomer used to form the polymer.

The "glass transition temperature," $T_g$, is the temperature at which an amorphous polymer or the amorphous domains of a semicrystalline or block co-polymer change from a brittle, vitreous state to a solid deformable state (or rubbery state) at atmospheric pressure. In other words, the $T_g$ corresponds to the temperature where the onset of segmental motion in the backbone chains of the polymer occurs. The measured $T_g$ of a given polymer can be influenced by the thermal history, and potentially pressure history, of the polymer, as well as the parameters utilized to measure the $T_g$, such as the pressure at which the measurement is made and the heating rate in differential scanning calorimetry (DSC). $T_g$ is a function of the chemical structure of the polymer, but is also affected by other compounds mixed with the polymer, whether it is a filler, solvent, etc.

The "melting temperature," $T_m$, of a polymer is the temperature at which an endothermal peak is observed in a DSC measurement, and where at least some of the crystallites begin to become disordered. The measured melting temperature may occur over a temperature range as the size of the crystallites, as well as presence of impurities and/or plasticizers, impacts the measured melting temperature. Crystalline domains are those in which polymer chains adopt an ordered orientation with segments of separate chains or of the same chain becoming essentially parallel to one another to form structures known as lamellae. Lamellae initially form from a point of nucleation. The formed lamellae then grow outward from the nucleation point to form larger, essentially spherical crystalline structures known as crystallites.

As used herein, a reference to the crystallinity of a polymer refers to the crystallinity as determined by standard DSC techniques with a heating rate of 20° C./min. For PLLA, it is assumed that a perfect crystal has a heat of fusion of 93.7 joules per gram.

A "polymer melt," refers to a semicrystalline polymer that has no or substantially no crystallites and is at or above the melting temperature, or for an amorphous polymer, is at a temperature sufficiently high enough above the glass transition temperature that it may be processed. As used herein a polymer melt is not necessarily 100% polymer but may include additives such as stabilizers, plasticizers, etc.

As used herein a construct, tube, etc which is said to be "fabricated from a polymer" or reference is made to a polymer construct, polymer tube, or polymeric tube or the like, the item so modified is made from a polymer, a blend of polymers, a material for which one or more polymers forms a continuous phase, or a material for which one or more polymers comprises at least 50% by volume of the material.

"Strength" refers to the maximum stress along an axis which a material will withstand prior to fracture. The ultimate strength is calculated from the maximum load applied during the test divided by the original cross-sectional area.

"Modulus" may be defined as the ratio of a component of stress or force per unit area applied to a material divided by the strain along an axis of applied force that results from the applied force. The modulus typically is the initial slope of a stress-strain curve at low strain in the linear region. For example, a material has a tensile, a compressive modulus, and a storage or shear modulus.

"Toughness" is the amount of energy absorbed prior to fracture, or equivalently, the amount of work required to fracture a material. One measure of toughness is the area under a stress-strain curve from zero strain to the strain at fracture. The units of toughness in this case are in energy per unit volume of material. See, e.g., L. H. Van Vlack, "Elements of Materials Science and Engineering," pp. 270-271, Addison-Wesley (Reading, Pa., 1989).

"Polymer melt relaxation" time as used herein is that determined utilizing a capillary viscometer. The polymer melt is forced out of the capillary with a piston at a temperature and pressure corresponding to extrusion conditions. Once these conditions have equilibrated in the rheometer, the piston movement is stopped. The melt relaxation time is defined as the time that it takes for the pressure to decay to 20% of its original value.

The terms "biodegradable," "bioabsorbable," and "bioerodable" are used interchangeably and refer to polymers and/or other materials that are capable of being completely degraded and/or eroded when exposed to bodily fluids such as blood and can be gradually resorbed, absorbed, and/or eliminated by the body. The processes of breaking down and absorption of the polymer can be caused by, for example, hydrolysis and metabolic processes. Biostable refers to polymers and/or materials that are not biodegradable.

As used herein, the terms poly(D,L-lactide), poly(L-lactide), poly(D,L-lactide-co-glycolide), and poly(L-lactide-co-glycolide) are used interchangeably with the terms poly(D,L-lactic acid), poly(L-lactic acid), poly(D,L-lactic acid-co-glycolic acid), and poly(L-lactic acid-co-glycolic acid), respectively.

EXAMPLES

The examples set forth below are for illustrative purposes only and are in no way meant to limit the invention. The following examples are given to aid in understanding the invention, but it is to be understood that the invention is not limited to the particular examples. The parameters and data are not to be construed to limit the scope of the embodiments of the invention.

Example 1

A number of extrusion trials were run with poly(L-lactide) to produce extruded polymer tubes. Poly(L-lactide) (PLLA), RESOMER® L 210 S, supplied by Boehringer Ingelheim, was used. The PLLA had a weight average molecular weight in the range of about 590,000 to about 650,000, a number average molecular weight in the range of about 320,000 to about 380,000, a crystallinity of about 60%, an inherent viscosity of 3.3-4.3 dL/g as determined in chloroform at 25° C. and a 0.1% (mass/volume) concentration, and a water content of less than or equal to 0.5%. The PLLA resin was dried in an on-line hopper using air at 60° C. and about 0% humidity resulting in a residual moisture content of less than 200 ppm. After being dried in the hopper, the PLLA was gravity fed to the extruder. The PLLA was extruded in a 1" inch Killion single screw extruder with a length to diameter ratio of 24 using a compression ratio of 3.27:1, and a speed (extruder screw) ranging from 5 to 15 RPM. The three zones of the extruder were set to 410° F. and the pressure in the extruder ranged from 2000 psi to 5100 psi with the 5100 psi occurring at the end of the third zone.

At the end of the extruder, the polymer melt was forced through a breaker plate prior to going through the spiral-cross-head die assembly. The spiral cross-head was manufactured by Guill Tool and Engineering company and was a Model 712 Crosshead, an earlier version than the 712 Model Assembly of Example 2. The die used had a 0.179" diameter. The temperature in the die and cross head assembly was about 430° F., and the pressure at the die exit was about 200 to about 700 psi.

The extruded film was drawn at a ratio ranging from 4 to 10 and cooled in a vacuum size chilled water bath at ambient temperature (about 20 to 25° C.) with a residence time in the water bath of about 30 seconds or less than 30 seconds. The air gap between the die exit and the water bath varied from 0 to 2".

Analysis of the thermal properties of a number of the polymer tubes (sample size of three for each test run) are summarized in Table 1. The data was obtained using a Differential Scanning Calorimeter at a heating rate of 20° C./min, with a flow of an inert and calibrated with an Indium standard. Crystallinity was determined based upon the area of the crystalline melting peak with 93.7 joules/gram as the reference value for a 100% crystalline PLLA polymer.

TABLE 1

Thermal Analysis Results for Polymer Tubes

| Test Run Number | Average Tg | Standard Deviation Tg | Average % Crystallinity | Standard Deviation % Crystallinity |
|---|---|---|---|---|
| 8 | 57.62 | 0.13 | 3.90 | 1.61 |
| 9 | 57.93 | 0.29 | 6.85 | 1.19 |
| 10 | 58.01 | 0.25 | 6.67 | 1.46 |
| 1 | 56.14 | 1.05 | 1.27 | 0.39 |
| 7 | 57.73 | 0.77 | 1.06 | 1.36 |
| 16 | 57.43 | 0.44 | 0.7 | 0.08 |

As shown in Table 1, all of these samples exhibited crystallinity under 10%, with some samples exhibiting crystallinity of less than 2%.

Example 2

The following prophetic example illustrates the extrusion of a polymer tube on slightly different equipment. Extrusion of PLLA as described in Example 1 is performed. The polymer resin is dried using a hopper/dryer as described in Example 1. The extruder used is a ¾" American Khune Extruder with a barrier screw, three feed flights, and a length to diameter ratio of 24:1. The extrusion is carried out at a compression ratio of 3:1 and a speed in the range of 5 to 30 RPM. The temperature in the extruder is about the same as or slightly lower than the temperatures used in Example 1.

At the end of the extruder, the polymer melt is forced through a breaker plate and into the spiral cross-head die assembly. The spiral cross-head is manufactured by Guill Tool and Engineering company and is a Model 712 Assembly which was selected for use with poly(L-lactide). The Model 712 Assembly primarily differs from that of example 1 in that the tip (analogous to reference numeral 3 in FIG. 3) is slightly different, being part Guill Tool and Engineering part No. 71203058 versus part No. 71203067. A die of 0.179" diameter is used. The temperature and pressure is about the same as in Example 1.

The extruded film is drawn and quenched as described in Example 1. The crystallinity of the resulting polymer tube is determined by DSC.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of forming a stent comprising:
heating and mixing a polymer comprising poly(L-lactide) (PLLA) in an extruder to form a polymer melt;
forming a tube from the polymer melt, the forming of the tube comprising conveying the polymer melt through the extruder into a die assembly to form a film, and after the film exits the die assembly, cooling and drawing the film to form the polymer tube, wherein the tube is cooled to below a glass transition temperature (Tg) of the polymer;
wherein the die assembly comprises an inlet for the polymer melt and a conical section that fits into a structure having a conical bore,
wherein the polymer melt flows through a spiral channel downstream of the inlet which is formed by spiral grooves in the conical section and a surface of the conical bore, the spiral channel cross-section gradually tapering as the polymer melt moves downstream,
wherein the spiral channel merges with an annular passage way between surfaces of the conical section and the conical bore to allow the polymer melt to flow through the spiral channel downstream into the annular passage way,
wherein a clearance between the surfaces of the conical section and the conical bore increases as the spiral channel tapers and merges with the annular passage way and when the tapering spiral channel merges with the annular passage way, some of the polymer melt spills over an edge of the spiral grooves into the annular passage way which changes the direction of polymer melt flow,
wherein the spiral channel and annular passage way provide for a balanced flow through the die assembly,
wherein the polymer melt flows from the annular passage way to an outlet of the die assembly, and
wherein the crystallinity of the polymer in the formed tube after cooling is not more than 5%;
wherein spiral flow provided by the spiral channel and the balanced flow allow for the crystallinity of not more than 5%,
processing the polymer tube at a temperature below the Tm of the polymer to increase the radial strength of the polymer tube and increase the crystallinity of the polymer tube from not more than 5% to a crystallinity in the range of about 20% to about 50%,
wherein the processing is at a temperature between 60 and 100° C. to provide crystallinity with small crystallite domains which contribute to both the strength and fracture toughness of the polymer of the polymer tube; and
forming a stent from the processed polymer tube,
wherein the crystallinity of the polymer tube prior to processing of not more than 5% allows for the increase in crystallinity of the tube to be formed in one step under processing conditions that enhance facture toughness.

2. The method of claim 1, wherein the grooves are substantially equally spaced around the circumference of the conical surface comprising the grooves.

3. The method of claim 1, wherein the processing comprises radially expanding the polymer tube which increases radial strength and the crystallinity of the polymer tube.

4. The method of claim 1, wherein the radial expansion occurs at a temperature in the range of 60° C. to 80° C.

5. The method of claim 1, wherein cooling the film comprises quenching the film to form the polymer tube.

6. The method of claim 1, wherein the crystallinity of the formed tube is not more than 4%.

7. The method of claim 6, wherein the crystallinity of the formed tube is not more than 3%.

8. The method of claim 1, wherein the heating and mixing of the polymer in the extruder occurs at about 190° C. to about 225° C.

9. The method of claim 8, wherein the extruder is operated at a compression ratio in the range of about 3.5:1 to about 2.75:1, and the maximum pressure in the extruder is in the range of about 4500 psi to about 5500 psi.

10. The method of claim 1, wherein the die assembly comprises a flow passage way comprising the inlet to receive the polymer melt from the extruder and at least two minor flow paths connected to the inlet with a dividing wedge between the two minor flow paths to divide the polymer melt.

11. The method of claim 10, wherein the inlet of the passage way receives the polymer melt from the extruder and wherein the passage way comprises at least two minor flow passage ways connected to the inlet with a dividing wedge between the two minor flow paths to divide the polymer melt.

12. The method of claim 1,
wherein the heating and mixing of the polymer in the extruder occurs at about 190° C. to about 225° C.; and
wherein the extruder is operated at a compression ratio in the range of about 3.5:1 to about 2.75:1, and the maximum pressure in the extruder is in the range of about 4500 psi to about 5500 psi.

* * * * *